United States Patent [19]

Debabov et al.

[11] Patent Number: 6,165,756

[45] Date of Patent: *Dec. 26, 2000

[54] **BACTERIAL STRAIN OF *ESCHERICHIA COLI* BKIIM B-3996 AS THE PRODUCER OF L-THREONINE**

[75] Inventors: Vladimir Georgievich Debabov; Jury Ivanovich Kozlov; Evgeny Moiseevich Khurges; Vitaly Arkadievich Livshits; Nelli Isaakovna Zhdanova; Mikhail Markovich Gusyatiner; Alexandr Konstantinovich Sokolov; Tatyana Alexandrovna Bachina; Nikolai Kazimirovich Yankovsky; Jury Dmitrievich Tsygankov; Andrei Jurievich Chistoserdov; Tatyana Grigorievna Plotnikova; Irina Clegovna Shakalis; Alla Valentinovna Belareva; Raisa Alexandrovna Arsatiants; Albert Fedorovich Sholin; Tamara Mikhailovna Pozdnyakova, all of Moscow, Russian Federation

[73] Assignee: Ajinomoto Co., Inc., Tokyo, Japan

[ * ] Notice: This patent is subject to a terminal disclaimer.

[21] Appl. No.: 09/390,701

[22] Filed: Sep. 7, 1999

Related U.S. Application Data

[62] Continuation of application No. 08/890,199, Jul. 9, 1997, Pat. No. 5,976,843, which is a continuation of application No. 08/633,028, Apr. 16, 1996, Pat. No. 5,705,371, which is a continuation of application No. 08/430,455, Apr. 28, 1995, Pat. No. 5,631,157, which is a continuation of application No. 08/336,563, Nov. 9, 1994, Pat. No. 5,538,873, which is a continuation of application No. 07/872,141, Apr. 22, 1992, abandoned, which is a division of application No. 07/499,278, filed as application No. PCT/SU88/00207, Oct. 25, 1988, Pat. No. 5,175,107.

[30] Foreign Application Priority Data

Dec. 9, 1988 [BE] Belgium .................................. 8801386
Dec. 15, 1988 [FR] France .................................. 88 16570

[51] Int. Cl.$^7$ .............................. C12N 1/21; C12N 15/70; C12P 13/08
[52] U.S. Cl. ..................... 435/116; 435/252.33; 435/472
[58] Field of Search .............................. 435/41, 106, 115, 435/252.3, 252.33, 252.8, 471, 472, 479

[56] References Cited

U.S. PATENT DOCUMENTS

| | | | |
|---|---|---|---|
| 5,175,107 | 12/1992 | Debabov et al. | .................. 435/252.33 |
| 5,538,873 | 7/1996 | Debabov et al. | ........................ 435/115 |
| 5,631,157 | 5/1997 | Debabov et al. | .................. 435/252.33 |
| 5,705,371 | 1/1998 | Debabov et al. | ........................ 435/115 |
| 5,976,843 | 11/1999 | Debabov et al. | ........................ 435/115 |

*Primary Examiner*—George C. Elliott
*Assistant Examiner*—Thomas G. Larson
*Attorney, Agent, or Firm*—Oblon, Spivak, McClelland, Maier & Neustadt, P.C.

[57] ABSTRACT

A bacterial strain of *Escherichia coli* BKIIM B-3996, a producer of L-threonine, containing a recombinant plasmid pVIC40 and deposited on Nov. 19, 1987 in the collection of microorganism cultures at the USSR Antiobiotics Research Institute under Reg. No. 1867.

12 Claims, 1 Drawing Sheet

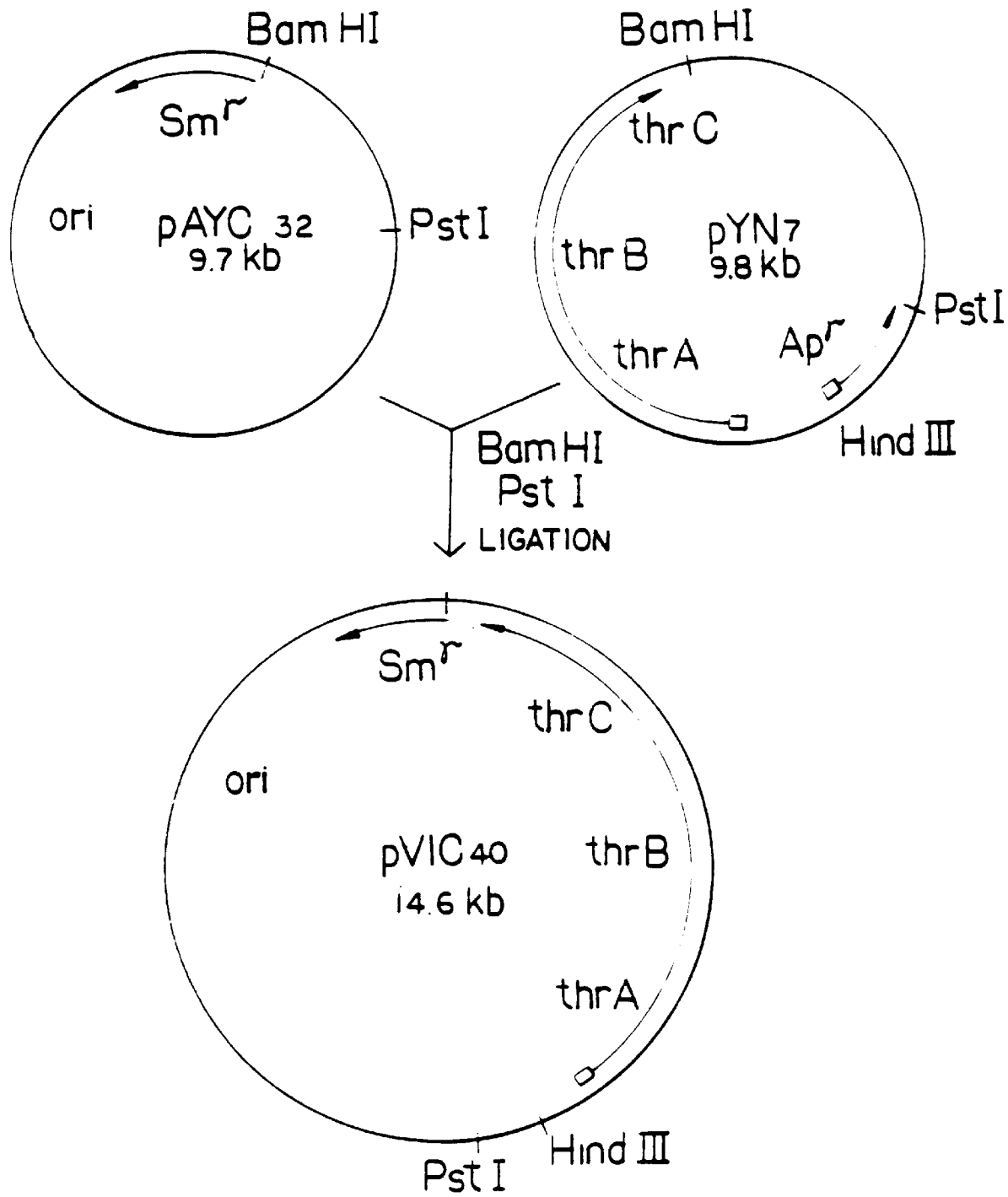

BACTERIAL STRAIN OF *ESCHERICHIA COLI* BKIIM B-3996 AS THE PRODUCER OF L-THREONINE

This application is a Continuation of application Ser. No. 08/890,199 filed on Jul. 9, 1997 now U.S. Pat. No. 5,976,843, which is a continuation of application Ser. No. 08/633,028 filed on Apr. 16, 1996, now U.S. Pat. No. 5,705,371, which is a continuation of application Ser. No. 08/430,455 filed on Apr. 28, 1995, now U.S. Pat. No. 5,631,157 which is a continuation of application Ser. No. 08/336,563 filed on Nov. 9, 1994, now U.S. Pat. No. 5,538,873, which is a continuation of application Ser. No. 07/872,141 filed on Apr. 22, 1992, now abandoned, which is a divisional application Ser. No. 07/499,278 filed on Jun. 12, 1990, now U.S. Pat. No. 5,175,107, which is a 371 of PCT/SU88/00207 filed on Oct. 25, 1988.

TECHNICAL FIELD

The present invention relates generally to microbiological industry and more specifically it concerns a novel bacterial strain of *Escherichia coli* BKIIM B-3996 as the producer of L-threonine.

L-threonine is known to be an essential amino acid applicable as the component of diverse nutritive mixtures of medical use. Besides, L-threonine can be used as an additive to animals' fodder, as well as a reagent for the pharmaceutical and chemical industries and as a growth factor for microorganisms producing some other amino acids, such as L-lysine and L-homoserine.

BACKGROUND ART

Known in the present state of the art are the L-threonine producing strains of microorganisms of a variety of species (e.g., *Brevibacterium flavum, Serratia marcescens, Escherichia coli*, and others). It is the mutating strains of *E. coli* whose cells contain hybrid plasmids carrying the genes of the threonine operon (U.S. Pat. Nos. 4,278,785; 4,321,325) that prove to be the most officacious L-threonine producers, of which the most productive is *Escherichia coli* strain VNIIgenetika M-1 (U.S. Pat. No. 4,321,325), which contains multicopy plasmid pYN7 obtained on the base of vector pBR322 and incorporating the threonine operon of *E. coli* strain K12 resistant to alpha-amino-beta-hydroxyvaleric acid, an analogue of threonine. The genes of the threonine operon of plasmid pYN7 code a bifunctional enzyme, viz., aspartate-kinase-homoserinedehydrogenase, which is insensitive to inhibition with L-threonine. Said strain M-1 is capable of accumulating L-threonine till a concentration of 30 g/l for a 40-hour fermentation period in laboratory fermenters when cultivated under conditions of feeding a sugar-ammonia additive to the nutrient medium in response to a signal sent by the pH sensor.

The aforesaid strain is featured by low productivity and inadequate stability of the plasmid, which compels one to make use of antibiotics to retain the plasmid in course of fermentation.

SUMMARY OF THE INVENTION

The strain proposed herein is a novel one and has not so far been described in literature.

It is therefore a primary and essential object of the present invention to provide a novel bacterial strain, which enables one to attain a high yield of L-threonine obtained within a shorter period of fermentation without adding any antibiotics during said period and featuring a high stability of the plasmid.

The aforesaid object is accomplished due to the fact that, according to the invention, proposed herein is a novel bacterial strain of *Escherichia coli* BKIIM B-3996 as the L-threonine producer, said strain containing recombinant plasmid pVIC40 and deposited on Nov. 19, 1987 in the collection of microorganism cultures at the USSR Antibiotics Research Institute under Reg. No. 1867.

The strain proposed herein is instrumental in producing 85 g/l L-threonine for a 36-hour fermentation period. The proposed strain contains recombinant plasmid pVIC40, which carries the same fragment of the *E. coli* chromosome as the pYN7 plasmid of the heretofore-known *E. coli* strain VNIIgenetika M-1 that codes the genes of L-threonine biosynthesis, and imparts to the cells resistance to an antibiotic streptomycin. Unlike the pYN7 the novel plasmid remains persistently in the cells when growing under nonselective conditions.

BRIEF DESCRIPTION OF THE FIGURE

The FIGURE schematically describes the preparation of the plasmid pVIC40.

BEST MODE OF CARRYING OUT THE INVENTION

The hereinproposed strain has been produced in several stages from the heretofore-known *E. coli* strain VNIIgenetika M-1.

At the first stage of the strain construction a genetic determinant of saccharose assimilation is transferred to said strain by virtue of transduction by bacteriophage P1 grown on a saccharose assimilating strain. The thus-obtained transformant is capable of utilizing saccharose and saccharose-bearing substrates, such as molasses, as the source of carbon.

At the second stage spontaneously arisen mutants capable of growing on a minimal medium M9, containing inhibitory concentrations of L-threonine (5 mg/ml), are taken out of the saccharose-assimilating transformant. One of such mutants, viz., *E. coli* VNIIgenetika-472T23 (which was deposited in the USSR Collection of Commercial Microorganisms at the USSR Antibiotics Research Institute under Reg. No. BKIIM B-2307), which has become resistant not only to L-threonine but also to L-homoserine is used for further selection.

At the third stage a transductant is obtained in said *E. coli* strain VNIIgenetika 472T23 with the aid of transduction by bacteriophage P1, which has been grown on a mutant of *E. coli* strain K12 having insertion of transposon Tn5 into gene tdh that codes an enzyme threoninedehydrogenase engaged in degradation of L-threonine, said transductant being devoid completely of activity of said enzyme. The thus-obtained transductant VNIIgenetika-TДГ-6 (deposited in the USSR Collection of Commercial Microorganisms at the USSR research Institute of Genetics and Selection of Commercial Microorganisms under Reg. No. BKIIM B-3420) has lost ability to cause degradation of the L-threonine being produced.

Further on, the VNIIgenetika TДГ-6 strain is deprived of a spontaneously arisen clone devoid of characteristics determined by plasmid pYN7, since the cells of said clone have lost said plasmid. The novel producer has been obtained as a result of genetic transformation of the cells of a plasmid-free variant of the VNIIgenetika TДГ-6 strain by the plasmid pVIC40.

Novel hybride plasmid pVIC40 has been produced by processing the heretofore-known plasmid pYN7 (U.S. Pat. No. , 4,278,765), as well as a broad-host range vector plasmid pAYC32 (cf. Chritoserdov A. Y., Tsygankov Y. D., Broad-host range vectors derived from a PSF 1010 Tnl plasmid, Plasmid, 1986, v.16, pp. 161–167), which is a derivative of the known plasmids pRSF 1010 and pBR 322 and featured by high persistence E. coli in cells,, by restrictases BamH1 and Pst1, followed by treatment with polynucleotideligase. The result mixture, after having been ligated, is used for transformation of the cells of the aforesaid plasmid-free variant of the VNIIgenetika- TⅡ-6 strain deficient in L-threonine, whereupon the colonies of transformants are taken out on the minimal agar-doped medium M9 devoid of L-threonine but containing streptomycin (100 µg/ml). It is from the cells of one of such transformants that plasmid pVIC40 is isolated, having a molecular mass of 9.7 mD. The pVIC40 plasmid incorporates the following fragments:

BamH1-Pst1 of a fragment of broad-host range vector plasmid pAYC 32, containing 7.6 thousand base pairs, said fragment comprising a gene if resistance to streptomycin;

BamH1-Pst1 of a fragment of plasmid pYN7, containing 7 thousand base pairs, said fragment comprising genes of the threonine biosynthesis of E. coli (threA, thrB, thrC).

Plasmid pVYC40 incorporates unique identification segments for restrictases BamH1 and Pst1.

The proposed strain exhibits the following cultural-morphological and biochemical features.

Cytomorphology. Gram-negative weakly-motile rods having rounded enus. Longitudinal size, 1.5 to 2 µm.

Cultural features.

Beef-extract agar. After 24 hours of growth at 37° C. produces round whitish semitransparent colonies 1.5 to 3 mm in diameter, featuring a smooth surface, regular or slightly wavy edges, the centre is slightly raised, homogeneous structure, pastelike consistency, readily emulsifiable.

Luria's agar. After a 24-hour growth at 37° C. develops whitish semitranslucent colonies 1.5 to 2.5 mm in diameter having a smooth surface, homogeneous structure, pastelike consistency, readily emulsifiable.

Minimal agar-doped medium M9. After 40 to 48 hours of growth at 37° C. forms colonies 0.5 to 1.5 mm in diameter, which are coloured greyish-white, semitransparent, slightly convex, with a lustrous surface.

Growth in a beaf-extract broth. Specific cultivation rate at 37° C. 1.3 h$^{-1}$. After a 24-hour growth exhibits strong uniform cloudiness, has a characteristic odour.

Physiological and biochemical features.

Grows upon thrust inoculation in a beef-extract agar. Exhibits good growth throughout the inoculated area. The microorganism proves to be a facultative anaerobe.

It does not liquefy gelatin.

Features a good growth on milk, accompanied by milk coagulation.

Does not produce indole.

Temperature conditions. Grows on bear-extract broth at 43° C. and below, an optimum temperature lying within 37 and 38° C.

pH value of culture medium. Grows on liquid media having the pH value from 6 to 8, an optimum value being 7.0.

Carbon sources. Exhibits good growth on saccnarose, glucose, fructose, lactose, mannose, galactose, xylose, glycerol, mannitol to produce an acid and gas.

Nitrogen sources. Assimilates nitrogen in the form of ammonium, nitric acid salts, as well as from some organic compounds.

Resistant to streptomycin, L-threonine and L-homoserine.

L-isoleucine is used as a growth factor.

Content of plasmids. The cells contain multi-copy hybrid plasmid pVIC40 (molecular mass 9.7 megadalton) ensuring resistance to streptomycin and carrying the genes of the threonine operon.

Aminoacetone formation. No acetone formation when growing in the presence of L-threonine.

Plasmid stability. The proposed strain is featured by increased ability to retain the plasmid when growing without a selective pressure aimed at maintaining the plasmid.

The process for producing L-threonine, using the herein-proposed novel producer strain is carried into effect as follows. The culture of E. coli strain BKIIM B-3996 is grown on an agar-doped medium M9 with streptomycin, whereupon a liquid inoculation medium is seeded with the resultant suspension of the grown cells. The medium contains a source of carbon and nitrogen, indispensable mineral salts, as well as a nutrient additive in the form of hydrolyzates of protein substrates, though the use of such an additive in the fermentation medium is fucultative. The incolumn is grown under conditions of a contstant controlled pH value of the medium (6.8 to 7.2) at 36 to 38° C. under continuous aeration and stirring. The thus-prepared inoculum or a suspension of cells washed out of the agar medium is used for seeding the fermentation medium, containing a source of carbon and nitrogen, mineral salts, as well as a nutrient additive in the form of hydrolyzates of protein substrates, since in cases of low inoculation doses said additive makes it possible to cut down the duration of fermentation, while in the case of high inoculation doses use of such an additive is facultative.

The fermentation process is carried out in fermenters equipped with a pH value constant control system, at a pH value of from 6.8 to 7.2 and a temperature of 36 to 38° C. under constant aeration and stirring. Used as a pH value maintaining agent is either ammonia liquor or a sugar-ammonia additive balanced in carbon and nitrogen. Duration of fermentation depends on the inoculation dose and degree of enriching the fermentation medium with growth factors and can vary from 24 to 50 hours. A total of 70 to 85 g/l L-threonine is accumulated towards the end of the fermentation process. The specific consumption of a carbon source for synthesis of one gram of L-threonine equals 2 to 2.3 g.

No plasmids are lost during fermentation.

To promote understanding given below are some specific examples of cultivation of the proposed strain and a schematic diagram illustrating a method for constructing the novel plasmid pVIC40, contained in the proposed strain.

EXAMPLE 1

The bacterial strain of Escherichia coli BKIIM B-3996 is grown on an agar-doped medium M9, containing saccnarose (9.2 mass percent) and streptomycin (100 µg/ml). The cells grown within a two-day period are suspended in a 0.9-percent sodium chloride solution, and 10 ml of said suspension having a titer of $10^8$ is used for seeding 500 ml of the inoculation medium of the following composition (in mass percent):

| | |
|---|---|
| saccharose | 4.0 |
| $(NH_4)_2SO_4$ | 0.5 |

-continued

| | |
|---|---|
| KH$_2$PO$_4$ | 0.2 |
| MgSO$_4$.7H$_2$O | 0.04 |
| FeSO$_4$.7H$_2$O | 0.002 |
| MgSO$_4$.5H$_2$O | 0.002 |
| yeast autolyzate | 0.02 |
| water | to make 100 percent. |

The inoculum is grown for 20 hours in laboratory fermenters having a capacity of 1.2 l under aeration (0.5 l/min) and stirring at a speed of 1000 rpm at 37° C. The pH value is maintained automatically within 6.9±0.2, using ammonia liquor. Then 50 ml of the thus-grown inoculum having a titre of 7 to 8·10$^9$ is used for seeding the fermentation medium (500 ml). The composition of the fermentation medium is the same as that of the inoculation medium, with the sole exception that the saccharose concentration equals 3 mass percent and 0.06 mass percent of sodium chloride is added thereto.

The fermentation process occurs in a laboratory fermenter having a capacity of 1.2 l under aeration (0.5 l/min) and stirring at a speed of 1200 rpm at a cultivation temperature of 37° C. The pH value is maintained within 6.9±0.2 by automatic feeding of a sugar-ammonia additive, which is in fact a mixture of a 70-percent saccharose solution and a 25-percent ammonia liquor, taken in a volumetric ratio of 3.6:1. The fermentation process lasts 36 hours to obtain a total of 85 g/l L-threonine. The proportion of cells which have lost plasmids is below one percent.

EXAMPLE 2

The cultivation process of the proposed strain is carried out in a way similar to that described in Example 1, but the grown inoculum is diluted with a 0.9-percent sodium chloride solution to obtain a titre of 10$^2$, whereupon one millilitre or such a suspension is used for seeding 500 ml of the fermentation medium having a composition similar to that described in Example 1, but having an increased yeast autolyzate (up to 0.5 mass percent). The fermentation process is conducted under conditions similar to those described in Example 1 for 50 hours.

The result is L-threonine in a concentration of 79 g/l, the proportion of cells which have lost plasmids being below one percent.

INDUSTRIAL APPLICABILITY

The proposed strain finds application in production of an essential amino acid L-threonine used for preparing medical-use nutritive mixtures, as a fodder additive of animals, as a reagent for the pharmaceutical and chemical industries, and as a growth factor for microorganisms producing other amino acids, such as L-lysine, and others.

What is claimed is:

1. An *E. coli* strain which produces L-threonine, derived by a process comprising the steps of:
   (i) transducing *E. coli* strain with a first bacteriophage P1 bearing genetic material necessary for saccharose assimilation, and
   (ii) isolating a transductant capable of utilizing saccharose or a saccharose-bearing substrate as a source of carbon.

2. The *E. coli* strain of claim 1, further derived by a process comprising the steps of:
   (iii) transducing said transductant with a second bacteriophage P1, and
   (iv) isolating a transductant lacking threonine dehydrogenase activity.

3. The *E. coli* of claim 2, wherein said second bacteriophage P1 bears a mutant threonine dehydrogenase-encoding gene whose gene product is devoid of threonine dehydrogenase activity.

4. The *E. coli* of claim 2, wherein said second bacteriophage P1 was obtained by growning bacteriophage P1 on a mutant *E. coli* strain devoid of threonine dehydrogenase activity and bearing a mutation in the threonine dehydrogenase-encoding gene.

5. A method for deriving an *E. coli* strain which produces L-threonine, said method comprising the steps of:
   (i) transducing *E. coli* strain with a first bacteriophage P1 bearing genetic material necessary for saccharose assimilation, and
   (ii) isolating a transductant capable of utilizing saccharose or a saccharose-bearing substrate as a source of carbon.

6. The method of claim 5, further comprising the steps of:
   (iii) transducing said transductant with a second bacteriophage P1, and
   (iv) isolating a transductant lacking threonine dehydrogenase activity.

7. The method of claim 6, wherein said second bacteriophage P1 bears a mutant threonine dehydrogenase-encoding gene whose gene product is devoid of threonine dehydrogenase activity.

8. The method of claim 6, wherein said second bacteriophage P1 was obtained by growning bacteriophage P1 on a mutant *E. coli* strain devoid of threonine dehydrogenase activity and bearing a mutation in the threonine dehydrogenase encoding gene.

9. A method for producing L-threonine, comprising using an *E. coli* strain derived by a method comprising the steps of:
   (i) transducing *E. coli* strain with a first bacteriophage P1 bearing genetic material necessary for saccharose assimilation, and
   (ii) isolating a transductant capable of utilizing saccharose or a saccharose-bearing substrate as a source of carbon.

10. The method of claim 9, said derivation further comprising the steps of:
    (iii) transducing said transductant with a second bacteriophage P1, and
    (iv) isolating a transductant lacking threonine dehydrogenase activity.

11. The method of claim 10, wherein said second bacteriophage P1 bears a mutant threonine dehydrogenase-encoding gene whose gene product is devoid of threonine dehydrogenase activity.

12. The method of claim 10, wherein said second bacteriophage P1 was obtained by growning bacteriophage P1 on a mutant *E. coli* strain devoid of threonine dehydrogenase activity and bearing a mutation in the threonine dehydrogenase-encoding gene.

* * * * *

UNITED STATES PATENT AND TRADEMARK OFFICE
CERTIFICATE OF CORRECTION

PATENT NO. : 6,165,756

DATED : December 26, 2000

INVENTOR(S): Vladimir Georgievich Debabov, et al.

It is certified that an error appears in the above-identified patent and that said Letters Patent is hereby corrected as shown below:

On title page, Item [30], the Foreign Application Priority Data should be deleted. No Priority has been claimed in this Application.

Signed and Sealed this

Twenty-ninth Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO.    : 6,165,756  
DATED         : December 26, 2000  
INVENTOR(S)   : Vladimir Georgievich Debabov et al.

Page 1 of 1

It is certified that error appears in the above-identified patent and that said Letters Patent is hereby corrected as shown below:

<u>Title page,</u>
Item [30], Foreign Application Priority Data, should be deleted.

Signed and Sealed this

Eighteenth Day of May, 2004

JON W. DUDAS
*Acting Director of the United States Patent and Trademark Office*